United States Patent

Hauck et al.

[11] 4,156,723
[45] May 29, 1979

[54] PERHYDRO NAPHTHALENE PENTOL DERIVATIVES

[75] Inventors: Frederic P. Hauck, Bridgewater; Michael E. Condon, Lawrenceville; Joyce Reid, Dayton, all of N.J.

[73] Assignee: E. R. Squibb & Sons, Inc., Princeton, N.J.

[21] Appl. No.: 821,889

[22] Filed: Aug. 4, 1977

[51] Int. Cl.² ............... A61K 31/13; A61K 31/495
[52] U.S. Cl. .................. 424/244; 546/206; 560/256; 260/239 B; 260/326.46; 260/326.5 C; 260/563 P; 424/246; 424/250; 424/267; 424/248.55; 424/248.57; 424/274; 424/311; 424/325; 544/59; 544/171; 544/173; 544/398; 544/399
[58] Field of Search .............. 260/268 BC; 560/256; 424/250, 244; 544/398

[56] References Cited

U.S. PATENT DOCUMENTS 3,894,031  7/1975  Hauck et al. ............... 260/268 BC
3,984,419  10/1976  Hauck et al. ............... 560/256

Primary Examiner—Paul M. Coughlan, Jr.
Attorney, Agent, or Firm—Lawrence S. Levinson; Merle J. Smith; Burton Rodney

[57] ABSTRACT

Compounds are provided having the structure

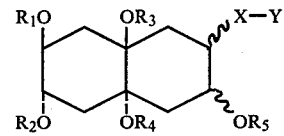

wherein $R_1$, $R_2$, $R_3$ or $R_4$ is hydrogen or acyl, and $R_5$ is hydrogen or acyl, X is a straight or branched bivalent alkylene radical and Y is

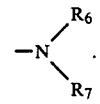

These compounds are useful in the treatment of hypertension.

15 Claims, No Drawings

PERHYDRO NAPHTHALENE PENTOL DERIVATIVES

COMPOUNDS OF THE INVENTION

The present invention relates to perhydro naphthalene derivatives which have a lowering effect on blood pressure and are useful in the treatment of hypertension, in mammalian species, for example, rats and dogs. In addition, the compounds of the invention can be employed as antibiotics. A compound of formula I (below) as well as its physiologically acceptable acid salts may be compounded according to pharmaceutical practice in oral or parenteral dosage forms such as tablets, capsules, elixirs, injectables or powders for administration of about 100 mg to 400 mg per day, preferably 125 mg to 175 mg per day, in 2 to 4 divided doses.

Furthermore, the compounds of this invention are useful as water softeners.

The compounds of the invention have the general formula:

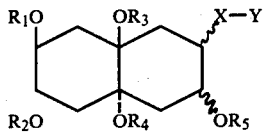

wherein $r_1$, $R_2$, $R_3$ and $r_4$ represent hydrogen or acyl, and $R_5$ is hydrogen or acyl, X is a single bond or a straight or branched chain bivalent alkylene radical, and Y is

$R_6$ and $R_7$ may be the same or different, representing hydrogen, acyl, lower alkyl, halo-lower alkyl, monocyclic cycloalkyl, monocyclic cycloalkyl-lower alkyl, hydroxy-lower alkyl, monocyclic aryl, monocyclic aryl-lower alkyl, monocyclic heterocyclic.

The

group may also form a heterocyclic radical.

X represents a single bond or a straight or branched chain bivalent alkylene hydrocarbon group having from one to about ten carbon atoms in the normal chain, such as an alkylene group of the structure $(CH_2)_n$ wherein n is one to ten, such as methylene, ethylene, propylene, trimethylene, butylene, dimethylethylene, and the like. Furthermore, X can correspond to any of the lower alkyl groups exemplified hereinafter; $R_1$, $R_2$, $R_3$, $R_4$ and/or $R_5$ and $R_6$ and/or $R_7$ may be an acyl radical of a carboxylic acid of less than twelve carbon atoms, which may be exemplified by the lower alkanoic acids (e.g., formic, acetic, propionic, butyric, valeric, trimethyl acetic and caproic acids), the lower alkenoic acids (e.g., acrylic, methacrylic, crotonic, 3-butenoic and sensciolo acids), the monocyclic arylcarboxylic acids (e.g., benzoic and toluic acids), the monocyclic aryl-lower alkanoic acids [e.g., phenacetic, β-phenylbutyric, and 5-(p-methylphenyl)- pentanoic acids], the cycloalkylcarboxylic acids (e.g., cyclobutanecarboxylic acid, cyclopentanecarboxylic acid and cyclohexanecarboxylic acid), the cycloalkenylcarboxylic acids (e.g., 2-cyclobutene carboxylic acid and 3-cyclopentenecarboxylic acid), the cycloalkyl and cycloalkenyl-lower alkanoic aids [e.g., cyclohexaneacetic, α-cyclopentanebutyric, 2-cyclopenteneacetic and 3-(3-cyclohexene)-pentenoic acid], and the like.

The alkanoic acids may include halogen substituents, for example, trifluoroacetic acid. In addition, other acyl groups which can be employed are angeloyl, veratroyl, vanilloyl, erythro-2-hydroxy-2-methyl-3-acetoxybutyryl, (1)-2-methylbutyryl; (d)-2-hydroxy-2-methylbutyryl; (d)-threo-2,3-dihydroxy-2-methylbutyryl and (1)-erythro-2,3-dihydroxy-2-methylbutyryl.

The term "lower alkyl" as employed herein includes both straight and branched chain radicals of up to eight carbon atoms, for instance, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, and the like.

Alkyl radicals substituted by F, Br, Cl or I are encompassed by the term halo-lower alkyl. Trifluoromethyl is a preferred halo-lower alkyl radical.

The term "monocyclic aryl" as employed herein contemplates monocyclic carbocyclic aryl radicals, for instance, phenyl and substituted phenyl radicals, such as lower alkyl phenyl (e.g., o-, m- or p-tolyl, ethylphenyl, butylphenyl, and the like), di(lower alkyl)phenyl (e.g., 2,4-dimethylphenyl, 3,5-diethylphenyl, and the like), halophenyl (e.g., chlorophenyl, bromophenyl, iodophenyl, fluorophenyl), o-, m- or p-nitrophenyl, dinitrophenyl, (e.g., 3,5-dinitrophenyl, 2,6-dinitrophenyl, and the like), trinitrophenyl (e.g., picryl).

The term "monocyclic aryoyl" includes any of the above aryl groups linked to a carbonyl group.

The term "monocyclic cycloalkyl" and "monocyclic cycloalkenyl" includes cyclic radicals containing from 3 to 6 ring members (e.g., cyclopropyl, cyclobutyl, cyclopentyl, cyclohexyl, cyclobutenyl and cyclohexenyl).

As indicated hereinbefore,

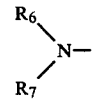

may form a heterocyclic radical. The symbols $R_6$ and $R_7$ may together represent the carbon (and hydrogen) and the oxygen, sulfur or nitrogen atoms which, with the nitrogen or carbon atoms in the above group, form a 5-, 6- or 7-membered nitrogen heterocyclic containing not more than one hetero atom in addition to the nitrogen already shown in the group and less than 21 atoms in the radical (excluding hydrogen). The heterocyclic radicals may include one to three substituents including lower alkoxy or lower alkyl as defined hereinafter; trihalomethoxy, such as trifluoromethoxy; trihalomethylmercapto, such as trifluoromethyl mercapto; N,N-dialkylsulfamoyl groups, such as N,N-dimethylsulfamoyl; lower alkanoyl groups as defined hereinafter such as acetyl, propionyl, and the like; hydroxy; hydroxy-lower alkyl, such as hydroxymethyl, 2-hydroxyethyl, or the like; hydroxy-lower alkoxy-lower alkyl, such as 2-(2-hydroxyethoxy)- ethyl, or the like; alkanoyloxy containing an alkanoyl as defined herein; alkanoyloxy-lower alkyl (up to about 14 carbons in the alkanoyl group), such as 2-heptanoyloxyethyl; carbo-lower alkoxy, such as carbomethoxy, carboethoxy, carbopropoxy, or the like; or 2-(alkanoyloxy-lower alkoxy) lower alkyl (with up to about 14 carbons in the alkanoyl group), such as 2-(decanoyloxyethoxy)-ethyl, or the like.

Illustrative of the heterocyclic radicals represented by R$_6$, R$_7$ or

are the following: piperidino; (lower alkyl)piperidino [e.g., 2-, 3-, or 4-(lower alkyl)-piperidino or 4-(N-lower alkyl)piperidino such as 2-(ethyl)-piperidino or 4-(N-isopropyl)-piperidino]; di(lower alkyl)-piperidino [e.g., 2,4-, 2,5- or 3,5-di(lower alkyl)piperidino such as 2,4-dimethylpiperidino or 2,5-di-t-butyl piperidino]; (lower alkoxy) piperidino [e.g., 2-methoxypiperidino or 3-methoxypiperidino]; hydroxypiperidino [e.g., 3-hydroxy- or 4-hydroxypiperidino]; aminomethyllpiperidino [e.g., 4-aminomethylpiperidino]; pyrrolidino; (lower alkyl)pyrrolidino [e.g., 3-methylpyrrolidino]; di(lower alkyl) pyrrolidino [e.g., 3,4-dimethylpyrrolidino]; (lower alkoxy)pyrrolidino [e.g., 2-methoxypyrrolidino]; morpholino; (lower alkyl)- morpholino [e.g., 3-methylmorpholino]; di(lower alkyl)- morpholino [e.g., 3,5-dimethylmorpholino]; (lower alkoxy)- morpholino [e.g., 2-methoxymorpholino]; thiamorpholino; (lower alkyl)thiamorpholino [e.g., 3-methylthiamorpholino]; di(lower alkyl)thiamorpholino [e.g., 3,5-dimethylthiamorpholino]; (lower alkoxy)thiamorpholino [e.g., 3-methoxy thiamorpholino]; piperazinol (lower alkyl) piperazino [e.g., N$^4$-methylpiperazino]; di(lower alkyl)piperazino [e.g., 2,5-dimethylpiperazino or 2,6-dimethylpiperazino]; (lower alkosy)piperazino [e.g., 2-methoxypiperazino]; (hydroxy-lower alkyl)-piperazino [e.g., N$^4$-(2-hydroxyethyl)-piperazino]; (alkanoyloxy-lower alkyl)piperazino wherein the alkanoyloxy group has up to 14 carbons [e.g., N$^4$-(2-heptanoyloxyethyl)piperazino or N$^4$-(2-dodecanoyloxyethyl)piperazino]; (hydroxy-lower alkoxy-lower alkyl)-piperazino [e.g., (hydroxy-methoxy-methyl)-piperazino]; (carbo-lower alkoxy)piperazino [e.g., N$^4$-(carbomethoxy-, carboethoxy-, or carbopropoxy)-piperazino]; homopiperazino; or N$^4$-(hydroxy-lower alkyl)homopiperazino [e.g., N$^4$-(2-hydroxyethyl)-homopiperazino]; piperidyl; (lower alkyl)piperidyl [e.g., 1-, 2-, 3- or 4-(lower alkyl)piperidyl, such as 1-N-methylpiperidyl or 3-ethylpiperidyl]; di(lower alkyl)-piperidyl [e.g., 2,4-, 2,5-, or 3,5-di(lower alkyl)piperidyl wherein lower alkyl is methyl, ethyl, n-propyl, isopropyl, etc.]; lower alkoxy piperidyl [e.g., 3-methoxypiperidyl or 2-ethoxypiperidyl]; hydroxy piperidyl [e.g., 3-hydroxy- or 4-hydroxypiperidyl]; aminomethyl-piperidyl [e.g., 4-aminoethylpiperidyl]; pyrrolidyl; lower alkyl pyrrolidyl [e.g., 1-N-methylpyrrolidyl]; di(lower alkyl)pyrrolidyl [e.g., 2,3-dimethylpyrrolidyl]; lower alkoxy pyrrolidyl [e.g., 4-N-methoxypyrrolidyl]; morpholinyl; (lower alkyl)morpholinyl [e.g., 3-methylmorpholinyl]; di(lower alkyl) morpholinyl [e.g., 3-methyl-4-N-ethylmorpholinyl]; (lower alkoxy)morpholinyl [e.g., 2-ethoxymorpholinyl]; thiamorpholinyl; (lower alkyl) thiamorpholinyl [e.g., 3-ethylthiamorpholinyl]; di(lower alkyl)thiamorpholinyl [e.g., 3-methyl-4-N-ethylthiamorpholinyl]; ;lower alkoxy thiamorpholino [e.g., 3-methoxythiamorpholinyl]; piperazinyl; alkyl, dialkyl, alkoxy or hydroxy-lower alkyl substituted piperazinyl.

The N-oxides of the compounds of formula I wherein Y represents a nitrogen containing heterocyclic radical can be formed by reacting such formula I compounds with a peracid such as m-chloroperoxy benzoic acid, perbenzoic acid or mono-perphthalic acid in a suitable solvent such as chloroform.

The compunds of formula I form acid addition salts by reaction with various inorganic and organic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such a hydrochloride, hydrobromide and hydroiodide, especially the first two, other mineral acids salts such as phosphate, sulfate, nitrate, etc., organic acid salts such as oxalate, tartrate, malate, maleate, citrate, pamoate, fumarate, camphorsulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodidel benzyl halides, such as benzyl chloride; and dilower alkyl sulfates, such as dimethyl sulfate. To form the quaternary ammonium salts, the free base initially formed is intereacted with at least one equivalent of the desired alkylating agent.

Preferred are those compounds wherein X is (CH$_2$)$_2$ or (CH$_2$)$_3$, Y is an amino group, a piperidino group or piperazino group with or without substituents and R$_1$, R$_2$, R$_3$, R$_4$ and R$_5$ are hydrogen or acyl. Most preferred are those compounds wherein X is (CH$_2$)$_2$, Y is dimethylamino,

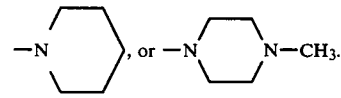

In all of the compounds of the invention, the OR$_1$, OR$_2$, OR$_3$ and OR$_4$ groups are axial and OR$_1$ and OR$_2$ are in trans configuration and OR$_3$ and OR$_4$ are in trans configuration.

The compounds of formula I include all stereoisomers and mixtures thereof. Thus,  X-Y can be cis or trans to OR$_3$ and   OR$_5$ can be cis or trans to X-Y.

The compounds of formula I of the invention wherein X is CH$_2$CH$_2$ may be prepared by reacting a tetrahydrofuran (lactone) compound of the structure

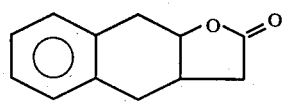

with an amine of the structure

 III in a molar ratio of II:III of within the range of from about 1:2 to about 1:3; at a temperature within the range of from about 50° to about 100° C., in the presence of an inert solvent, such as tetrahydrofuran, dioxane 1,2-dimethoxyethane, diethyl ether and the like to form a naphthalenol compound of the structure

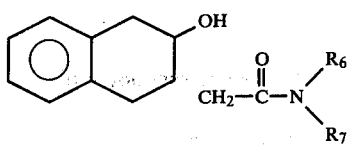 IV

The formula IV compound is reduced by reaction with a reducing agent, such as lithium aluminum hydride, preferably under nitrogen and in the presence of an inert solvent, such as tetrahydrofuran, dioxane, diethyl ether and the like to form a compound of the structure

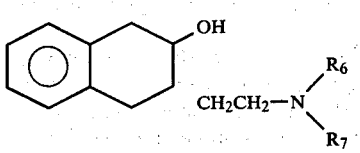 V

The formula V compound is converted to the corresponding diene VI by reacting with a reducing metal, such as lithium or sodium in liquid ammonia in the presence of a proton source, such as a lower alcohol to form the corresponding diene of the structure

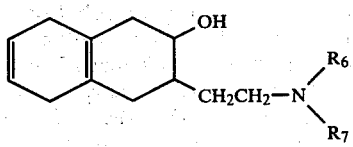 VI

The diene VI is then converted to the compound of the invention in the manner described hereinafter.

The compounds of formula I of the invention wherein X is a single bond, that is compounds of the structure

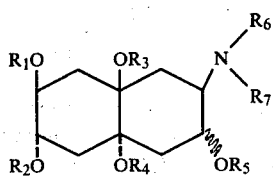 VII may be prepared by reacting an epoxide of the structure

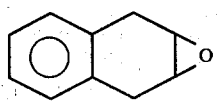 VIII with an amine

 III to form a compound of the structure

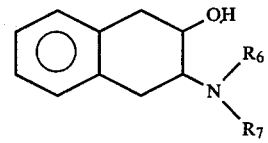 IX

The formula IX compound is then converted to the corresponding diene X by reacting IX with a reducing metal, such as sodium or lithium in liquid ammonia in the presence of a proton source, such as a lower alcohol to form the corresponding diene

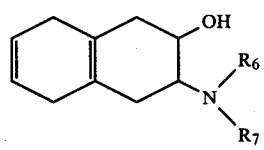 X which is converted to the compounds of formula I of the invention as described hereinafter.

The compounds of formula I of the invention wherein X represents methylene may be prepared by reacting amine XI with m-chloroperbenzoic acid to form the corresponding N-oxide XII

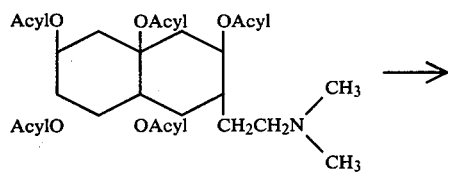 XI

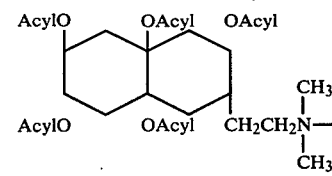 XII which is then heated to produce olefin XIII

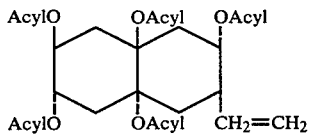 XIII

Oxidation of XIII with m-chloroperbenzoic acid yields oxirane XIV

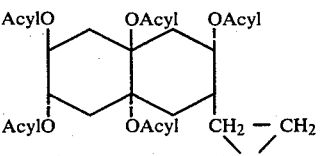 XIV which is oxidized with paraperiodic acid to yield aldehyde XV

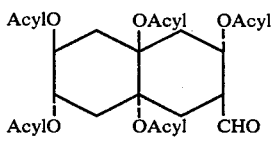

which is converted by reductive alkylation with amines to the desired product I wherein X=CH$_2$ and Y is

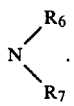

Alternatively, the compounds of formula I of the invention wherein X represents methylene or substituted methylene may be prepared by reaction of the epoxide

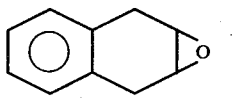

with diethylaluminum cyanide in the manner of Nagata JCS (c) 236S (1970), to form the corresponding nitrile

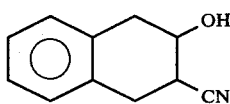

with is then reacted with LAH to form compounds of the structure

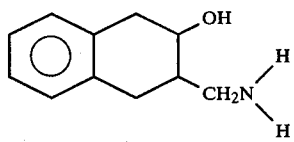

which can then be N-substitued by well-known procedures.

The formula XVII compounds may be converted to the corresponding diene in the manner as described hereinbefore.

The diene

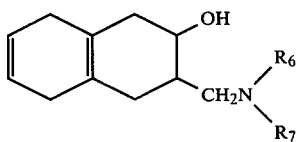

may be converted to the corresponding compounds of formula I of the invention in a manner as described hereinafter.

The compounds of the invention of formula I wherein X represents a straight or branched chain having the group (CH$_2$)$_{n'}$ wherein n' is 3 or more may be prepared by reacting an epoxide of formula VIII with a Grignard reagent of the structure

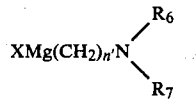

wherein X is Br or I. The compound so prepared, that is

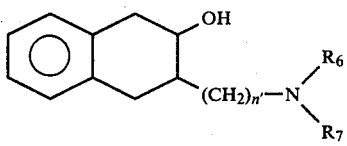

may be converted to the corresponding diene

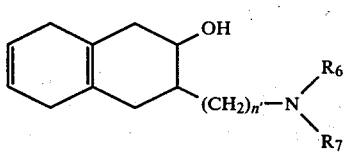

and thence to the compounds of formula I wherein X is an alkylene group which contains 3 or more carbons in the normal carbon chain employing procedures described herein.

The pentol of formula I of the invention wherein R$_1$, R$_2$, R$_3$, and R$_4$ are hydrogen, can be formed by hydroxylating any of the aforementioned dienes to the corresponding pentol, for example, by reacting the diene with formic acid, perchloric acid, and aqueous hydrogen peroxide, at temperatures ranging from about 20° to about 40° C. to form a mixture of esters, and then subjecting the mixture of esters to basic hydrolysis by dissolving the mixture of esters in a solvent boiling below about 100° C., such as a monohydric alcohol containing up to four carbon atoms (e.g., methyl alcohol, ethyl alcohol, propyl alcohol, isopropyl alcohol or butyl alcohol), and then treating the solution with a base, such as an alkali metal or alkaline earth metal hydroxide or alkoxide (e.g., sodium hydroxide, potassium hydroxide, barium hydroxide, calcium hydroxide, sodium methoxide or calcium diethoxide) and heating the mixture to temperatures ranging from about 40° to about 80° C., to form the pentol of the structure

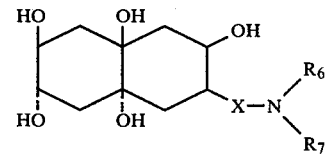

In the above reaction the hydrogen peroxide is employed in a molar ratio to the diene of within the range of from about 2.2:1 to about 15:1 and preferably from about 2.2:1 to about 5:1. The base is employed in a molar ratio to the mixture of esters of within the range of from about 2.2:1 to about 10:1 and preferably from about 2.2:1 to about 5:1.

The pentol of Formula XX can be converted to the corresponding penta ester, i.e., where R$_1$, R$_2$, R$_3$, R$_4$ and R$_5$ are acyl as defined hereinbefore, by reacting the pentol with an acylating agent, such as a hydrocarbon carboxylic acid containing less than twelve carbon atoms as discussed hereinbefore, the acid anhydride thereof, or corresponding acyl halide, and an acid catalyst, such as perchloric acid, at a temperature within the range of from about −20° to about 0° C. The acid, acid anhydride or acyl halide is employed in a molar ratio to the pentol of within the range of from about 5:1 to about 20:1 and preferably from about 5:1 to about 10:1 and the acid catalyst is employed in a molar ratio to the pentol of within the range of from about 1.1:1 to about 2:1 and preferably about 1.1:1 to about 1.5:1.

In an alternative procedure, the diene of formula VI can be converted to the corresponding pentol by dissolving the diene VI in an organic carboxylic acid having up to about eight carbon atoms, such as acetic acid, treating the mixture with a silver salt corresponding to the acid, such as silver acetate (in a molar ratio of diene to silver salt of within the range of from about 1:2 to about 1:4 and preferably about 1:2) and iodine (in a molar ratio of diene to iodine of 1:1), heating the reaction mixture at a temperature of within the range of from about 60° to about 110° and preferably from about 80° to about 100°C. to form a compound (depending on which acid and silver salt are employed) of the structure

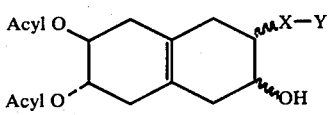

XXI

The above diester of the structure XXI can be converted to the corresponding pentol by dissolving the diester in a suitable protonic solvent, such as ethyl alcohol, treating the solution with an excess of an aqueous base, such as aqueous sodium hydroxide or potassium hydroxide, to effect hydrolysis to the corresponding triol of the structure:

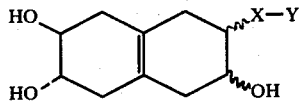

XXII

The above triol can be converted to the pentol by reacting with formic acid and hydrogen peroxide (as described hereinbefore), at temperatures ranging from about 20° to about 40° C., preferably about 35°, and then treating the mixture (free of solvent) with an alcohol and a base (as described hereinbefore) to form the pentol wherein OR's (1 to 4) are axial and each pair of OR's (1 and 2, and 3 and 4) are trans.

The pentols or derivatives thereof can also be prepared by reacting the diene

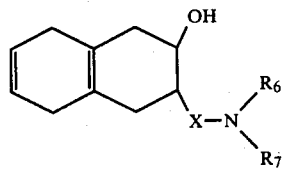

VI with formic acid and one equivalent of an oxidizing agent, such as aqueous hydrogen peroxide, and after removal of solvent, dissolving the residue in an alcohol-base as described hereinbefore to effect hydrolysis and form a triol olefin of the structure

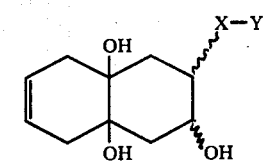

XXIII

The above triol olefin can then be converted to the pentol as described hereinbefore with respect to the conversion of the triol olefin XXII.

Where Y is $NH_2$, the pentols of the invention can be prepared by reacting an aminoalkyl tetrahydronaphthalene with a reducing agent, such as lithium ribbon in the presence of liquid ammonia, ethyl ether, and a proton source, such as a lower alcohol, to form a diene of the diene of the structure:

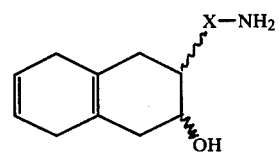

XXIV and reacting the diene with an acyl halide (wherein acyl and the halogen are as defined hereinbefore), such as benzoyl chloride, in a molar ratio of diene:halide of within the range of from about 1:1 to about 2:1 in a basic solvent, such as pyridine, triethylamine, or dilute base to form a diene of the structure

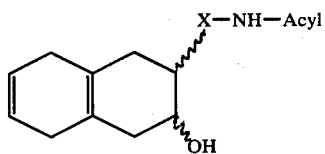

XXV and reacting the diene with formic acid and an oxidizing agent, such as hydrogen peroxide, and subjecting the product to basic hydrolysis (as described hereinbefore) to form an aminoalkyl pentol of the structure:

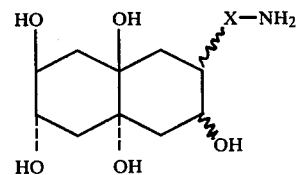

XXVI

The pentol tetraacylate of formula I, wherein $R_5$ is H, can prepared from the diene alcohol VI by conversion to the succinate half ester, A, using

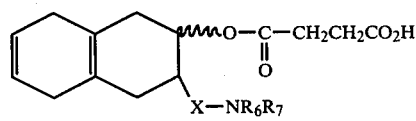

XXVII succinic anhydride in pyridine, converting this to a salt with a strong non-participating acid, such as perchloric, in a carboxylic acid, such as acet,c oxidizing with the peracid of the same carboxylic acid, such as peracetic acid, in a ratio of peracid to diene of about 2:1 to about 3:1, precipitating the oxidation product by addition of non-polar dileunts, such as benzene and ethyl ether, and acylating the crude oxidation product with the addition of the same carboxylic acid anhydride, such as acetic anhydride, to give, on dilution with ethyl ether, the tetra acyl succinate,

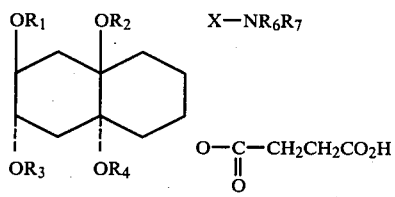
XXVIII

The tetraacyl succinate XXVIII can be converted to the pentol tetra acylate XXIX by dissolving in an aqueous solution of

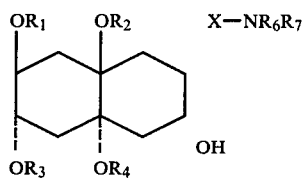
XXIX a weak base, such as sodium bicarbonate, and warming at temperatures from 40°–80° C. for a period of from 15 minutes to 1 hour.

The starting materials II

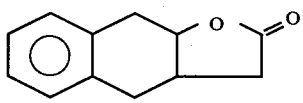
II may be prepared by reaction of the epoxide

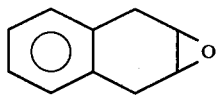
VIII with a diester, such as diethyl malonate in the presence of an alkali metal alkoxide, such as sodium ethoxide to form an ester lactone of the structure

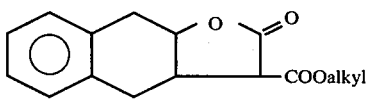
XXX

The ester lactone of structure XXX is hydrolyzed by reaction with a strong base, such as sodium hydroxide or potassium hydroxide in the presence of an aqueous lower alcohol solvent, and decarboxylated at 200° to form the compound of structure II.

The intermdiates of structures V, IX, XII, XIV, and XVII falling within the general structure

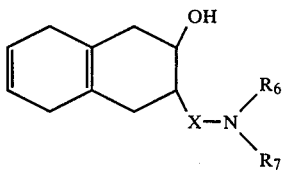
VI are novel compounds.

The following Examples illustrate the present invention without, however, limiting the same thereto. All temperatures are expressed in degrees Centrigrade.

EXAMPLE 1 trans-1,2,3,4-Tetrahydro-3-[2-(4-methyl-1-piperazinyl-)ethyl]-2-naphthalenol

A. 2,3,3a,4,9,9a-Hexahydro-2-oxonaphtho[2,3-b]-furan-3-carboxylic acid, ethyl ester Sodium ethoxide is prepared by adding 12.3 g (0.533 M) of sodium portionwise to 600 ml absolute ethanol in a nitrogen atmosphere. After the sodium is gone, 85.5 g (0.533 M) of diethyl malonate is added dropwise over a period of 15 minutes during which time the mixture is heated to reflux. After 5 minutes a solution of 77.8 g (0.533 M) of 2,3-epoxy-1,2,3,4-tetrahydronaphthalene in 125 ml absolute ethanol is added dropwise over a period of 45 minutes at reflux. Before the addition is complete a large amount of solid precipitates making stirring difficult. After refluxing 5 hours the mixture is cooled and the pH is adjusted to 6 by adding glacial acetic acid. Most of the ethanol is removed in vacuo, water is added and the mixture is extracted 4 times with ether. The combined ether extracts are washed with saturated NaCl solution, dried, and freed of solvent in vacuo leaving an orange oil. Ether is added and white crystalline material is deposited. This is harvested and washed with ether to give 46.4 g (33.4%) of the title ester lactone.

B. trans-3a,4,9,9a-Tetrahydronaphtho[2,3-b]furan2-3H)-one

A mixture of 35.9 g (138 mmol) of the ester lactone of Part A, 11.1 g (167 mmol) 85% KOH in 300 ml ethanol and 100 ml water is heated under reflux 45 minutes. After cooling most of the ethanol is removed in vacuo. Water is added and neutral material is removed by extracting once with ether. The aqueous layer is acidified with HCl and the acid lactone is extracted into ether. The combined ether extracts (3) are dried, filtered and most of the solvent is removed in vacuo.

The material is decarboxylated by heating in an oil bath. At ~190° the material becomes liquid and gas evolution is noted. The bath is held at 190°–210° until gas evolution ceases (~30 minutes). On cooling the material solidifies to give 23.7 g (91%).

C. trans-1,2,3,4-Tetrahydro-3-[2-(4-methyl-1-piperazinyl)-2-oxoethyl]-2-naphthalenol A mixture of 30.2 g (0.162 M) of the lactone of Part B and 32 g (0.32 M) N-methylpiperazine in 200 ml THF is heated under reflux over the weekend. The mixture is taken to dryness in vacuo leaving a brown oil which on standing in ether gives 33.8 g (72%) of crystalline amide.

D. trans-1,2,3,4-Tetrahydro-3-[2-(4-methyl-1-piperazinyl)ethyl]-2-naphthalenol

A mixture of 3.7 g (97.4 mmol) of lithium aluminum hydride in 50 ml THF is heated to reflux in a nitrogen atmosphere. A solution of 28.1 g (97.4 mmol) of amide in 100 ml of dry THF is added dropwise over a period of 1 hour. The mixture is heated under reflux overnight. After cooling the hydride is decomposed by dropwise addition of saturated Na₂SO₄ solution. The salts are removed by filtration and washed with ether. The filtrate is taken to near dryness in vacuo. Water is added and the mixture is extracted three times with ether. The ether extracts are dried, filtered and freed of solvent in vacuo leaving 21.4 g (80%) of yellow oil which solidifies on standing to give the title compound.

EXAMPLE 2 trans-1,2,3,4,5,8-Hexahydro-3-[2-(4-methyl-1-piperazinyl)ethyl]-2-naphthalenol

A solution of 25.4 g (92.7 mmol) of the amine of Example 1 in 100 ml ether is added to 1 liter liquid ammonia. Lithium (10.0 g) is added portionwise over a period of 10 minutes. After stirring 30 minutes, absolute ethanol is added dropwise until the color is discharged (140 ml added in 1 hour). More ether is added and the ammonia is boiled off. While cooling in an ice bath, the mixture is diluted with 1 liter water. The layers are separated and the aqueous is reextracted with ether. The combined organic layers are dried over $K_2CO_3$, filtered, and the solvent is removed in vacuo leaving 27 g of the title compound in the form of an oil.

EXAMPLE 3

Decahydro-7-[2-(4-methyl-1-piperazinyl)ethyl]-2,3,4a,6,8a-naphthalenepentol

The crude diene (92.7 mmol) is added slowly to 120 ml cold 88% formic acid. Perchloric acid (26.4 g of 70%, 185.4 mmol) is added. Hydrogen peroxide (50 ml of 30%) is then added over a period of 30 minutes (maintaining the temperature at 30°-35° with intermittant cooling). After addition is complete the temperature is allowed to rise to 45° and held at 35°-45° for 2 hours before the mixture is left stirring overnight in a large water bath at room temperature. Part of the solvent is removed in vacuo. Water is added and the mixture is again concentrated. This process is repeated three more times. Absolute ethanol (125 ml) is added to the residue and then, while cooling, a solution of 40 g KOH in 40 ml water is added. The mixture is heated on a steam bath 30 minutes. After cooling the dark brown mixture is diluted with 500 ml ice water. The aqueous mixture (pH 10) is extracted three times with ether and three times with ethyl acetate to give only ~1.2 g of material. The aqueous is then extracted 5 times with n-BuOH followed by a 24 hour continuous extraction with n-BuOH. The combined BuOH extracts are dissolved in 500 ml 95% EtOH, treated with 8 g 10% Pd/C and hydrogenated at up to 50 psi to remove any N-oxide present. Very little uptake is noted in 5 hours. The catalyst is removed by filtration and the solvent is removed in vacuo. The residue is dissolved in 50 ml MeOH and the solution is diluted with 200 ml EtOAc. Some salts are removed by filtration. The filtrate is taken to dryness in vacuo leaving 10.5 g of material. This is chromatographed on 300 g Activity 4 basic alumina using 20% MeOH in $CHCl_3$. The pentol is collected in fractions 2 and 3. The resulting viscous oil washed with ether and dried to give 1.8 g (5.6%) of the title compound.

EXAMPLE 4

Decahydro-7-[2-(4-methyl-1-piperazinyl)ethyl]-2,3,4a,6,8a-naphthalenepentol, pentaacetate ester (2β,3α,4aα,7α,8aβ)

The chromatographed pentol of Example 3 (1.8 g, 5.2 mmol) is dissolved in 20 ml acetic anhydride and 1 ml glacial acetic acid. The solution is cooled to −40° and treated with 2 ml 70% perchloric acid. The mixture is left overnight in the freezer. After cooling to −30°, 10 ml methanol is added dropwise over a period of 30 minutes. The cold mixture is poured into 60 ml cold concentrated $NH_4OH$. The mixture is immediately extracted twice with chloroform. The chloroform extracts are dried and freed of solvent in vacuo leaving 3.0 g yellow viscous material. On standing in ether-hexane 2.0 g (69%) of off white solid is deposited. Three recrystallizations from ethyl acetate-hexane (the first with a charcoal decolorization) gives the title compound, 420 mg shrinking 165°, m.p. 167°-169°.

EXAMPLE 5 trans-1,2,3,4-Tetrahydro-3-[2-(1-piperidinyl)ethyl]-2-naphthalenol

A. trans-1,2,3,4-Tetrahydro-3-[2-(1-piperidinyl)-2-oxoethyl]-2-naphthalenol

A mixture of 23.0 g (0.122 M) trans-3a-4,9,9a-tetrahydronaphtho[2,3-b]furan-2(3H)-one and 21.3 g (0.25 M) piperidine in 200 ml THF is heated under reflux over the weekend. On cooling, the material starts crystallizing. The solvent is removed in vacuo, ether is added and the white solid is harvested by filtration (27.7 g, 83%).

B. trans-1,2,3,4-Tetrahydro-3-[2-(1piperidinyl)ethyl]-2-naphthalenol, hydrochloride (1:1)

To a mixture of 3.84 g (101.3 mmol) of lithium aluminum hydride in 150 ml dry THF in a nitrogen atmosphere is added portionwise over a period of 30 minutes 27.7 g (101.3 mmol) of the solid amide of Part A. The mixture is heated under reflux overnight. After cooling the hydride is decomposed by dropwise addition of saturated $Na_2SO_4$ solution. When the gray color is gone the salts are removed by filtration and washed with THF and ether. The filtrate is taken to near dryness in vacuo. Water is added and the product is extracted into ether, dried and freed of solvent in vacuo leaving 24.8 g (94%) of the title compound.

EXAMPLE 6 trans-1,2,3,4-Tetrahydro-3-[2-(1-piperidinyl)ethyl]-2-naphthalenol, hydrochloride (1:1)

A 2.0 g sample of the free amine of Example 5 is converted to the hydrochloride by dissolving in ether and adding a solution of HCl in IPA. The white solid that precipitates is recrystallized from IPA to give the title compound, 1.8 g (79%), shrinking 184°, m.p. 189°-191°.

EXAMPLE 7 cis-3-[2-(1-piperidinyl)ethyl]-1,2,3,4,5,8-hexahydro-2-naphthalenol

A solution of 22.1 g (85.6 mmol) of trans-1,2,3,4-tetrahydro-3-[2-(1-piperidinyl)ethyl]-2-naphthalenol in 125 ml ether is added to 1 liter liquid ammonia. Lithium (10.0 g of rod) is added portionwise over a period of 10 minutes. After stirring 30 minutes, absolute EtOH is added dropwise until the color is discharged (170 ml and added in 75 minutes). More ether is added and the ammonia is boiled off. While cooling, 1 liter of cold water is added and the layers are separated. The aqueous is reextracted with ether and the combined organic layers dried and freed of solvent in vacuo to leave a quantitative yield of diene.

EXAMPLE 8

2,6,9a-cis-Decahydro-6-[2-(1-piperidinyl)ethyl]-2,3,4a,6,8a-naphthalenepentol

The diene (78.5 mmol) of Example 7 is added slowly to 120 ml cold 88% formic acid. Hydrogen peroxide (50 ml of 30%) is added dropwise over a period of 30 minutes maintaining the temperature at 35° or below with occasional cooling. After addition is complete the temperature is allowed to rise to 45° and held at 35°–45° for 2 hours before the mixture is left stirring overnight in a water bath at room temperature. The solution is taken to near dryness in vacuo. Water is added and removed in vacuo four times (until negative to starch — KI). The residue is dissolved in 125 ml of ethanol and treated with a solution of 40 g of KOH in 40 ml water. The dark solution is heated under reflux 30 minutes, cooled and diluted to 350 ml with ice water. Three ether extractions give 6.9 g of foam and four ethyl acetate extractions give an additional 13.9 g. On standing in EtOAc-MeOH the ethyl acetate extracts give 7.4 g crystalline material. Chromatography on Activity IV basic alumina of material from the mother liquor and the ether extract give an additional 4.7 g of crystalline material — total yield crystaline 12.1 g (47%). The two crops of crystalline material are ascertained to be the same isomer by comparison of m.p., TLC, NMR and by conversion of each of the pentaacetate and comparison of m.p. and NMR.

The crystalline material obtained directly (7.4 g) is recrystallized from EtOAc-MeOH with a charcoal decolorization to give the title compound, 6.5 g, m.p. 192°–196°.

EXAMPLE 9

2,6,8a-cis-Decahydro-6-[2-(1-piperidinyl)ethyl]-2,3,4a,6,8a-naphthalenepentol, pentaacetate ester 2,6,8a-cis-Decahydro-6-[2-(1-piperidinyl)ethyl]-2,3,4a,6,8a-naphthalenepentol (5.0 g, 15.2 mmol) is partially dissolved in 50 ml acetic anhydride and 4 ml of glacial acetic acid. The mixture is cooled to −30° and 4.5 ml 70% perchloric acid is added dropwise over a period of 10 minutes. The mixture is left in the freezer overnight. Methanol (25 ml) is then added dropwise over a period of 20 minutes while cooling at −15° to −25°. The mixture is poured into 150 ml cold concentrated NH$_4$OH and extracted twice with chloroform. The extracts are dried and freed of solvent. Hexane is added to the residue and white solid is harvested. This is recrystallized from ethyl acetatehexane to give the title compound, 7.3 g (89%), m.p. 167°–170°.

EXAMPLE 10 trans-3-[2-(Dimethylamino)ethyl]-1,2,3,4-tetrahydro-2-naphthalenol

A. trans-1,2,3,4-Tetrahydro-3-[2-dimethylamino2-oxoethyl]-2-naphthalenol

A mixture of 18.8 (0.10 mol) of trans-3a, 4,9,9a-tetrahydronaphtho[2,3-b]furan-2(3H)-one, 35 ml of anhydrous dimethylamine, and 35 ml of dry THF is heated in a small Parr bomb at 100° for 3 days. The cooled reaction mixture is then taken to dryness in vacuo, and the residue triturated with ether to give 22.5 g (97%) of crystalline solid after drying in vacuo.

B. trans-3-[2-(Dimethylamino)ethyl]-1,2,3,4-tetrahydro-2-naphthalenol

To a stirred slurry of 3.78 g (0.10 mol) of LiAlH$_4$ in 150 ml of dry THF is added 22.50 g (0.097 mol) of the above amide of Part A (solid) over 30 minutes, and the resulting mixture is refluxed overnight under nitrogen.

The reaction mixture is cooled to 0°–5°, the excess LiAlH$_4$ destroyed by dropwise addition of saturated aqueous Na$_2$SO$_4$, and the inorganic precipitate filtered off and washed with THF. The filtrate is concentrated in vacuo, the residue diluted with water, and this thoroughly extracted with ether. The combined extracts are washed with saturated aqueous NaCl, dried, and concentrated in vacuo to give 16.8 g (79%) of the title compound as an oil.

EXAMPLE 11 trans-3-[2-(Dimethylamino)ethyl]-1,2,3,4-tetrahydro-2-naphthalenol, hydrochloride (1:1)

A cooled solution of 1.7 g of the above oil of Example 10 in ether is treated with excess hydrogen chloride saturated isopropaneol, and the resulting solid filtered off and recrystallized from isopropanol to give the title compound, m.p. 166°–169°.

EXAMPLE 12 trans-3-[2-(Dimethylamino)ethyl]-1,2,3,4,5,8-hexahydro-2-naphthalenol

A solution of 14.6 g (66.6 mmol) of trans-3-[2-(diethylamino)ethyl]-1,2,3,4-tetrahydro-2-naphthalenol (prepared as in Example 10) in 125 ml of ether is added to 1 liter of NH$_3$ (liquid). To this stirred solution is added 10 g of Li in pieces over 10 minutes. When the addition is complete, the reaction mixture is stirred for 30 minutes, after which time absolute EtOH (∼150 ml) is added dropwise until the blue color is discharged. The NH$_3$ is then allowed to evaporate, the residue is diluted with water, and this thoroughly extracted with ether. The combined ether extracts are washed with saturated aqueous NaCl, dried, and concentrated in vacuo to 13.4 g (92%) of the title compound as an oil.

EXAMPLE 13 trans-3-[2-(Dimethylamino)ethyl]-1,2,3,4,5,8-hexahydro-2-naphthalenol, hydrochloride (1:1)

A solution of 1.4 g of the Example 12 oil in ether is treated with excess HCl saturated isopropanol. The resulting solid is filtered off, and directly recrystallized from isopropanol to afford the title compound (0.7 g), m.p. 186°–189°.

EXAMPLE 14

2,6,8a-cis-7-[2-(Dimethylamino)ethyl]decahydro-2,3,4a,6,8-a-naphthalenepentol trans-3-[2-(Dimethylamino)ethyl]-1,2,3,4,5,8hexahydro-2-naphthalenol (11.9 g, 53. 8 mmols) prepared as described in Example 12 is dissolved in 60 ml of cold 88% formic acid. Hydrogen peroxide (25 ml of 30%) is then added dropwise over 30 minutes, maintaining the temperature at 25°–35° with occasional cooling. The resulting solution is stirred overnight at room temperature.

The solution is then taken to near dryness in vacuo. Water is added and removed in vacuo (4 times —until negative starch-iodide obtained). The residue is dissolved in 100 ml of absolute EtOH, a solution of 25 g of KOH in 25 ml of water added, and this solution heated on a steam bath for 30 minutes.

The cooled solution is then added to ice water (~250 ml), NaCl added, and this extracted with ether (total ~500 ml).

The aqueous layer is then extracted with ethyl acetate (4X, ~800 ml total), the combined extracts dried, and concentrated in vacuo to a semi-solid residue, Trituration with EtOAc-MeOH gives 0.80 g of crude product.

The aqueous layer is then subjected to continuous extraction with EtOAc (3 days), and yield 2.5 g of crude product.

Continuous extraction with n-BuOH affords 13.6 g of a solid, which when digested repeatedly with EtOAc affords an additional 2.9 g of product.

The three fractions of crude product obtained as described above are combined (total = 6.2 g = 40%) and recrystallized from EtOAc-MeOH (charcoal decolorization) to give the title compound, 6.80 g), m.p. 189°–192°.

EXAMPLE 15

2,6,8a-cis-7-[2-(Dimethylamino)ethyl]decahydro-2,34a,6,8a-naphthalenepentol, pentaacetate ester To a stirred solution of 3.8 g (13.1 mmols) of the product of Example 14 in 40 ml of acetic anhydride and 4 ml of acetic acid at −30° is assed 4 ml of 70% HClO₃ over 5 minutes, and the resulting mixture stored in a freezer overnight.

MeOH (20 ml) is then added dropwise over 20 minutes to the above mixture at −20°, and the resulting mixture poured into 150 ml of cold concentrated NH₄OH. This is extracted with CHCl₃, the combined and extracts dried and concentrated in vacuo, and the residue triturated with hexane to give 4.5 g (69%) of crude product. Recrystallization from EtOHc-hexane gives the title compound (3.4 g), m.p. 172°–175°.

EXAMPLE 16 trans-1,2,3,4-Tetrahydro-3-(1-piperidinyl)-2-naphthalenol, hydrochloride (1:1)

2,3-Epoxy-1,2,3,4-tetrahydronapthalene (7.3 g, 50 mmol), 19 l ml (250 mol) isopropanol and 50 ml piperidine are charged to a small Parr bomb and heated at 120°–120+° for 4 days. After cooling the mixture is taken to dryness in vacuo leaving an amber oil which crystallizes on standing. This is recrystallized from a small amount of hexane to give (6.5 g, 56%) of a pale yellow solid melting 52°–58°. This solid is dissolved in ether and converted to the hydrochloride by adding a solution of HCl in isopropyl alcohol. The salt is removed by filtration and recrystallized twice from isopropyl alcohol-methyl alcohol to give the title compound 5.5 g (73%), m.p. 249°–252°.

EXAMPLE 17 cis-3-(1-Piperidinyl)-1,2,3,4,5,8-hexahydro-2-naphthalenol

A solution of 22.1 g (85.6 mmol) of trans-1,2,3,4-tetrahydro-3-(1-piperidinyl)-2-naphthalenol in 125 ml ether is added to 1 liter liquid ammonia. Lithium (10.0 g of rod) is added portionwise over a period of 10 minutes. After stirring 30 minutes absolute EtOH is added dropwise until the color is discharged (170 ml added in 75 minutes). More ether is added and the ammonia is boiled off. While cooling, 1 liter of cold water is added and the layers are separated. The aqueous portion is reextracted with ether and the combined organic layers dried and freed of solvent in vacuo to leave a quantitative yield of diene.

EXAMPLE 18

2,6,8a-cis-Decahydro-6-(1-piperidinyl)-2,3,4a,6,8a-naphthalenepentol

The diene (78.5 mmol) of Example 17 is added slowly to 120 ml cold 88% formic acid. Hydrogen peroxide (50 ml of 30%) is added dropwise over a period of 30 minutes maintaining the temperature at 35° or below with occasional cooling. After addition is complete the temperature is allowed to rise to 45° and held at 35°–45° for 2 hours before the mixture is left stirring overnight in a water bath at room temperature. The solution is taken to near dryness in vacuo. Water is added and removed in vacuo four times (until neg to starch — KI). The residue is dissolved in 125 ml of ethanol and treated with a solution of 40 g KOH in 40 ml water. The solution is heated under reflux 30 minutes, cooled and diluted to 350 ml with ice water. The resulting solution is extracted in ether, and ethyl acetate. On standing in EtOAc-MeOH the ethyl acetate extracts give the title compound in the form of a crystalline material. Chromatography on Activity IV basic alumina of material from the mother liquor and the ether extract give an additional amount of crystalline material. The crops of crystalline material are ascertained to be the same isomer by comparison of m.p., TLC, NMR and by conversion of each to the pentaacetate and comparison of m.p. and NMR.

EXAMPLE 19

2,6,8a-cis-Decahydro-6-(1-piperidinyl)-2,3,4a,6,8a-naphthalenepentol, pentaacetate ester 2,6,8a-cis-Decahydro-6-(1-piperidinyl)-2,3,4a,6,8a-naphthalenepentol (5.0 g, 15.2 mmol) is partially dissolved in 50 ml acetic anhydride and 4 ml of glacial acetic acid. The mixture is cooled to −30° and 4.5 ml 70% perchloric acid is added dropwise over a period of 10 minutes. The mixture is left in the freezer overnight. Methanol (25 ml) is then added dropwise over a period of 20 minutes while cooling at −15° to −25°. The mixture is poured into 150 ml cold concentrated NH₄OH and extracted twice with chloroform. The extracts are dried and freed of solvent. Hexane is added to the residue and white solid is harvested. This is recrystallized from ethyl acetatehexane to give the title compound.

EXAMPLE 20

2,6,8a-cis-Decahydro-6-[(1-piperidinyl)methyl]-2,3,4a,6,8a-naphthalene pentol, pentaacetate ester A. 2,6,8a-cis-7-[2-(Dimethylamino)ethyl]decahydro-2,3,4a,6,8a-naphthalenepentol, pentaacetate ester, N-oxide A solution of 8.5 g of 2,6,8a-cis-7-[2-(dimethylamino)ethyl]decahydro-2,3,4a,6,8a-naphthalenepentol, pentaacetate ester (prepared as in Example 15) in 200 ml of chloroform is cooled in an ice bath and 4.4 g of 85% m-chloroperbenzoic acid is added. The mixture is warmed to room temperature over 5 hours. The solution is partially evaporated in vacuo to one-third its volume and chromatographed on 400 g of neutral Alumina III (wet-packed in chloroform). The column is eluted with 600 ml of chloroform to remove any forerun and then the N-oxide product is eluted with 650 ml of 20% methanolic chloroform to give 10.4 g of oil. Crystallization from ethyl acetate gives the title A compound.

B. 7-Ethenyl-decahydro-2,3,4a,6,8a-naphthalenepentol, pentaacetate ester

An amount of 6.4 g the above N-oxide is heated in a vacuum distillation set-up under 30 mm Hg vacuum with nitrogen bleed until all the solid is melted and vigorous evolution of volatile side products cease. The vacuum is then improved to 2–3 mm Hg and the product distilled as a pale yellow liquid which crystallizes on standing to give 4.55 g of the olefin as a white solid.

C. 7-Oxiranyl-decahydro-2,3,4a,6,8a-napthalenepentol, pentaacetate ester

A solution of 2.0 g of the above pentaacetate-olefin and 1.05 g of 85% m-chloroperbenzoic acid in 50 ml of chloroform is prepared at 0° C. and stirred for about 16 hours at room temperature. The solution is then suction filtered through 30 g of neutral Alumina III. The alumina is washed with 100 ml of chloroform and the combined filtrate evaporated in vacuo to give a colorless oil, which solidifies on standing to give the epoxide product.

D. 7-Formyl-decahydro-2,3,4a,6,8a-naphthalenepentol, pentaacetate

A solution of 6 g pf paraperiodic acid ($2.62 \times 10^{-2}$m) in 18 ml of water is added to a solution of 4.8 g ($1.2 \times 10^{-2}$m) of pentaacetate-epoxide from part C in 70 ml of tetrahydrofuran and the solution stirred at room temperature for 2½ hours. The solution is then partitioned between chloroform (600 ml) and water (200 ml). The layers are separated and the aqueous layer is reextracted with chloroform. The combined chloroform extract is washed with saturated sodium bicarbonate solution, dried (MgSO$_4$) and evaporated in vacuo to give a solid. Analytical data (NMR, IR, and TLC) indicate that this material is ca. 75% the desired aldehyde.

E. 2,6,8a-cis-Decahydro-6-[(1-piperidinyl)methyl]-2,3,4a,6,8a-naphthalenepentol, pentaacetate ester An equimolar mixture of piperidine and the preceding aldehyde (Part D) in glacial acetic acid is reduced under 3 atm H$_2$ pressure in the presence of PtO$_2$ until uptake is complete. After filtration to remove catalyst, solvent is removed in vacuum. The residue is dissolved in water and carefully basified with dilute K$_2$CO$_3$ solution to yield the title compound.

EXAMPLE 21

2,6,8a-cis-7-[3-(Dimethylamino)propyl]decahydro-2,3,4a,6,8a-naphthalenepentol, pentaacetate A. trans-3-[3-(Dimethylamino)propyl]-1,2,3,4-tetrahydro-2-naphthalenol to a solution of 0.1 mol of dimethylamino propyllithium in 500 ml of ether cooled to 0°–5° C. is added dropwise a solution of 7.3 g (0.05 mol) of 2,3-epoxy-1,2,3,4-tetrahydronaphthalene in 100 ml of ether. The reaction mixture is then heated under reflux for 2 hours and decomposed with water. The organic layer is separated and dried and the desired 1,2,3,4-tetrahydro-3-(3-dimethylaminopropyl)-2-naphthalenol separated from byproducts by column chromatography on neutral alumina.

B. trans-3-[3-(Dimethylamino)propyl]-1,2,3,4,5,8-hexahydro-2-naphthalenol

A solution of 14.6 g (66.6 mmol) of trans-3-[3-(diethylamino)propyl]-1,2,3,4-tetrahydro-2-naphthalenol in 125 ml of ether is added to 1 liter of NH$_3$ (liquid). To this stirred solution is added 10 g of Li in pieces over 10 minutes. When the addition is complete, the reaction mixture is stirred for 30 minutes, after which time absolute EtOH (~ 150 ml) is added dropwise until the blue color is discharged. The NH$_3$ is then allowed to evaporate, the residue is diluted with water, and this thoroughly extracted with ether. The combined ether extracts are washed with saturated aqueous NaCl, dried, and concentrated in vacuo to 13.4 g (92%) of the title compound as an oil.

C. trans-3-[3-(Dimethylamino)propyl]-1,2,3,4,5,8-hexahydro-2-naphthalenol, hydrochloride (1:1)

A solution of 1.4 g of the compound of Part B in ether is treated with excess HCl saturated isopropanol, the resulting solid filtered off, and directly recrystallized from isopropanol to afford the title C compound.

D. 2,6,8a-cis7-[3-(Dimethylamino)propyl]decahydro-2,3,4a,6,8a-naphthalenepentol trans-3-[3-(Dimethylamino)propyl]-1,2,3,4,5,8-hexahydro-2-naphthalenol (11.9 g, 53.8 mmols) prepared as described in part B is dissolved in 60 ml of cold 88% formic acid. Hydrogen peroxide (25 ml of 30%) is then added dropwise over 30 minutes, maintaining the temperature at 25°–35° with occasional cooling. The resulting solution is stirred overnight at room temperature.

The solution is then taken to near dryness in vacuo. Water is added and removed in vacuo (4 times — until negative starch-iodide obtained). The residue is dissolved in 100 ml of absolute EtOH, a solution of 25 g of KOH in 25 ml of water added, and this solution heated on a steam bath for 30 minutes.

The cooled solution is then added to ice water (~250 ml), NaCl added, and this extracted with ether (total ~500 ml).

The aqueous layer is then extracted with ethyl acetate (4X, ~800 ml total), the combined extracts dried, and concentrated in vacuo to a semi-solid residue. Trituration with EtOAc-MeOH gives crude product.

The aqueous layer is then subjected to continuous extraction with EtOAc (3 days), and yields additional crude product.

Continuous extraction with n-BuOH affords additional solid, which when digested repeatedly with EtOAc affords additional product.

E. 2,6,8a-cis-7-[3-(Dimethylamino)propyl]decahydro-2,3,4a,6,8a-naphthalenepentol, pentaacetate ester To a stirred solution of 3.8 g (13.1 mmols) of the product of Part D in 40 ml of acetic anhydride and 4 ml of acetic acid at −30° is added 4 ml of 70% HClO$_3$ over 5 minutes, and the resulting mixture stored in a freezer overnight.

MeOH (20 ml) is then added dropwise over 20 minutes to the above mixture at −20°, and the resulting mixture poured into 150 ml of cold concentrated NH$_4$OH. This is extracted with CHCl$_3$, the combined extracts dried and concentrated in vacuo, and the residue triturated with hexane to give crude product. Recrystallization from EtOAc-hexane gives the title compound.

EXAMPLES 22 TO 35

Following the procedure of Examples 1 to 3 but substituting for N-methylpiperazine the compound listed in Column I of Table I set out below, the compound listed in Column II is obtained.

TABLE I

| Ex. No. | Column I | Column II |
|---|---|---|

Column II structure (applies to all rows unless noted):

Decahydronaphthalene with HO, OH substituents at positions shown, and CH₂CH₂N(R₆)(R₇) side chain; additional OH and HO, OH groups on the ring system.

Column I entries show HN(R₆)(R₇) or —N(R₆)(R₇):

22. HN(C₂H₅)₂ — as in Column I
23. HN(CH₃)(C₂H₅)
24. HN⟨―O―⟩ (morpholine)
25. HN⟨―N―CH₂CH₂OH⟩ (hydroxyethylpiperazine)
26. HN⟨ ⟩ (pyrrolidine)
27. HN⟨ ⟩ (piperidine)
28. HN⟨―N―C₂H₅⟩ (ethylpiperazine)
29. HN(CH₃)₂
30. HN⟨ ⟩ (azacycloheptane/hexamethyleneimine)
31. HN(C₆H₄S)₂ — bis(thiophenyl)amine type with two S-containing six-membered rings
32. HN(CH₂-C₆H₄S)₂ — with CH₂ linkers to S-containing rings
33. HN(C₆H₅)₂
34. HN(CH₂C₆H₅)₂
35. HN(CH₂CH₂OH)₂

EXAMPLES 36 TO 49

Following the procedure of Example 4, but substituting for the decahydro-7-[2-(4-methyl-1-piperazinyl)ethyl]-2,3,4a,6,8a-naphthalenepentol the compound listed in Column II of Table I of Examples 22 to 35, the pentaacetate ester of such compounds of Examples 22 to 35 is formed.

EXAMPLES 50 TO 61

Following the procedure of Examples 16 to 18 but substituting for the 1-piperidino compound the compound set out in Column I of Table II below, the compound set out in Column II is obtained.

TABLE II

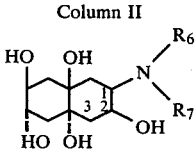

| Ex. No. | Column I | Column II |
|---|---|---|
| 50. | HN(CH$_3$)$_2$ | as in Column I |
| 51. | (piperidino) HN | |
| 52. | HN(CH$_3$)(C$_2$H$_5$) | |
| 53. | NH(CH$_3$)C$_4$H$_9$ | |
| 54. | (pyrrolidino) HN | |
| 55. | (morpholino) HN | |
| 56. | HN(CH$_2$CH$_2$OH)$_2$ | |
| 57. | HN(C$_6$H$_5$)$_2$ | |
| 58. | HN(CH$_2$C$_6$H$_5$)$_2$ | |
| 59. | (dithiolane) HN | |
| 60. | HN(piperazinyl)N—CH$_2$CH$_2$OH | |
| 61. | HN(piperidinyl)—CCH$_3$ (=O) | |

EXAMPLES 62 TO 73

Following the procedure of Example 19, but substituting for the 2,6,8a-cis-decahydro-6-(1-piperidinyl)-2,3,4a,6,8a-naphthalenepentol, the compound listed in Column I of Table II of Examples 50 to 61, pentaacetate ester of such compounds of Examples 50 to 61 is formed.

EXAMPLES 74 To 87

Following the procedure of Example 20, but substituting for piperidine, the compounds of Examples 36 to 49 as shown in Column I of Table III set out below, the compounds shown in Column II are obtained.

TABLE III

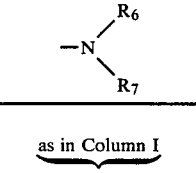

| Ex. No. | Column I | Column II |
|---|---|---|
| 74. | HN(C$_2$H$_5$)$_2$ | as in Column I |
| 75. | HN(CH$_3$)(C$_2$H$_5$) | |
| 76. | (morpholino) HN | |
| 77. | HN(piperazinyl)N—CH$_2$CH$_2$OH | |
| 78. | (pyrrolidino) HN | |
| 79. | (piperidino) HN | |
| 80. | HN(piperazinyl)N—C$_2$H$_5$ | |
| 81. | HN(CH$_3$)$_2$ | |
| 82. | (azepane) HN | |
| 83. | (dithiolane) HN | |
| 84. | HN(CH$_2$-S)(CH$_2$-S) | |
| 85. | HN(C$_6$H$_5$)$_2$ | |
| 86. | HN(CH$_2$C$_6$H$_5$)$_2$ | |
| 87. | HN(CH$_2$CH$_2$OH)$_2$ | |

EXAMPLES 88 TO 95

Following the procedure of Example 21 but substituting for dimethylaminopropyl lithium the aminoalkyl lithium compound shown in Column I of Table IV set out below, the compounds shown in Column II are obtained.

TABLE IV

| Ex. No. | Column I<br>Li(CH$_2$)$_{n'}$N(R$_6$)(R$_7$) | Column II<br>Decahydronaphthalene tetraol with (CH$_2$)$_{n'}$N(R$_6$)(R$_7$) substituent 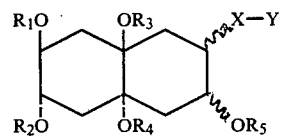 |
|---|---|---|
| 88. | Li(CH$_2$)$_4$N(CH$_3$)$_2$ | as in Column I |
| 89. | Li(CH$_2$)$_3$N⟨cyclohexyl⟩ | |
| 90. | Li(CH$_2$)$_3$N(CH$_3$)(C$_2$H$_5$) | |
| 91. | Li(CH$_2$)$_4$N⟨cyclopentyl⟩ | |
| 92. | Li(CH$_2$)$_6$N⟨morpholinyl⟩ | |
| 93. | Li(CH$_2$)$_9$N(C$_6$H$_5$)$_2$ | |
| 94. | Li(CH$_2$)$_3$N(CH$_2$C$_6$H$_5$)$_2$ | |
| 95. | Li(CH$_2$)$_3$N⟨dithiolane⟩ | |

EXAMPLES 96 TO 103

Following the procedure of Example 19, but substituting for the 2,6,8a-cis-decahydro-6-(1-piperidinyl)-2,3,4a,6,8a-naphthalenepentol, the compounds listed in Column I of Table II of Examples 88 to 95, the pentaacetate ester of such compounds of Examples 88 to 95 is formed.

EXAMPLE 104

2,3-trans-4a,8a-trans7[2-(Dimethylamino)ethyl]-decahydro-2,3,4a,6,8a-naphthalene pentol,2,3,4a,8a-tetraacetate A solution of 20 g of 1,2-trans-3-[2-(dimethylamino)ethyl]-1,2,3,4,5,8-hexahydro-2-naphthol (as prepared in Example 12) in 200 ml of pyridine is treated with 10 g of succinic anhydride. After standing for 1 day at 25° C., the solvent is evaporated, toluene added and evaporated, to yield the succinate half ester. This is taken up in 140 ml of glacial acetic acid and 20 ml of acetic anhydride, cooled to 10° C. in ice, and treated carefully with 7 ml of 70% perchloric acid. After stirring 15 minutes, the addition of 35 ml of 40% peracetic acid is carried out over ½ hours, at 15° C. The temperature is allowed to come to 25° C. for ½ hour, then the bath temperature is raised to 45° C. for 1 hour. The mixture is then cooled to 5° C. and diluted with 400 ml of benzene. The upper phase is discarded, and the treatment repeated twice with benzene and twice using ethyl ether. The resulting viscous oil is cooled to −15° C. and dissolved cautiously in 70 ml of acetic anhydride. Another ½ ml of 70% perchloric is added, and after 1 day at −15° C., another 70 ml of acetic anhydride. After two more days at −15° C., the mixture is diluted with 2 l. of ethyl ether and the resulting dark gum dissolved in water and rendered basic with sodium bicarbonate. This solution is extracted quickly with ethyl acetate, then the aqueous is warmed at 60°–80° C. on a steam cone for 45 minutes. The resulting mixture is extracted with chloroform, dried using magnesium sulfate, and evaporated to an oil.

Chromatography on neutral alumina, activity II, in ethyl acetate with increasing concentrations of methanol affords a fraction containing pure hydroxy tetraacetate.

What is claimed is:

1. A compound of the structure

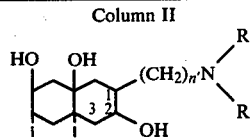

wherein R$_1$, R$_2$, R$_3$, and R$_4$ are the same and R$_5$ may be the same or different from R$_1$, R$_2$, R$_3$ and R$_4$, and R$_1$, R$_2$, R$_3$, R$_4$ and R$_5$ are selected from the group consisting of hydrogen or an acyl radical of a carboxylic acid of less than 12 carbons, X is a single bond or a straight or branched chain alkylene group of the structure (CH$_2$)$_n$ wherein n is 1 to 10, Y is

wherein R$_6$ and R$_7$ are the same or different and are selected from the group consisting of hydrogen, lower alkyl, trifluoromethyl, monocyclic cycloalkyl having 3 to 6 ring members, monocyclic cycloalkyl lower alkyl, wherein the cycloalkyl has 3 to 6 ring members, hydroxy-lower alkyl, phenyl, lower alkylphenyl, an acyl radical of a carboxylic acid of less than 12 carbons, di(lower alkyl)phenyl, halophenyl, mono-, di- or trinitrophenyl, phenyl lower alkyl, wherein lower alkyl contains 1 to 8 carbons, and

can be taken together to form a heterocyclic radical; wherein the heterocyclic radicals represented by

taken together contain 5-, 6- or 7-members in the heterocyclic ring, the ring being pyrrolidine, piperidine, morpholine, thiamorpholine, piperazine or homopiperazine, said heterocyclic ring containing 0 to 3 substituents selected from the group consisting of lower alkoxy, lower alkyl, trihalomethoxy, trihalomethylmercapto, N,N-dialkylsulfamoyl, lower alkanoyl, hydroxy, hydroxy-lower alkyl, hydroxy-lower alkoxy-lower alkyl, alkanoyloxy, alkanoyloxy-lower alkyl, carbo-lower alkoxy, or 2-(alkanoyloxy-lower alkoxy)lower alkyl, and stereoisomers thereof, physiologically acceptable acid salts thereof, physiologically acceptable quaternary salts thereof and N-oxides thereof.

2. A compound according to claim 1 wherein $R_1$, $R_2$, $R_3$, and $R_4$ are hydrogen or alkanoyl of 1 to 3 carbons.

3. A compound according to claim 2 wherein $R_1$, $R_2$, $R_3$, $R_4$ and $R_5$ are alkanoyl.

4. A compound according to claim 2 wherein $R_1$, $R_2$, $R_3$ and $R_4$ are acetyl.

5. A compound according to claim 2 wherein $R_1$, $R_2$, $R_3$, $R_4$ and $R_5$ are acetyl.

6. A compound according to claim 1 having the structure

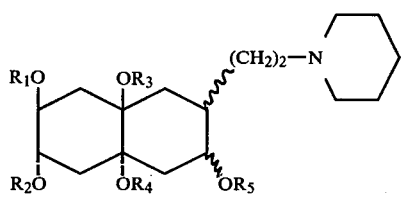

and stereoisomers thereof.

7. The compound according to claim 6 wherein $R_1$, $R_2$, $R_3$, $R_4$ and $R_5$ are acetyl and stereoisomers thereof.

8. The compound according to claim 6 wherein $R_1$, $R_2$, $R_3$, $R_4$ and $R_5$ are hydrogen.

9. The compound according to claim 1 having the structure

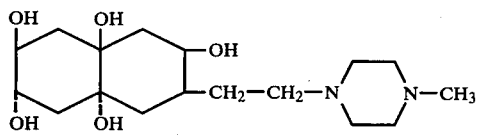

10. The compound according to claim 1 having the structure

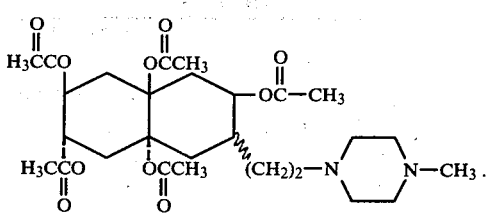

11. The compound according to claim 1 having the structure

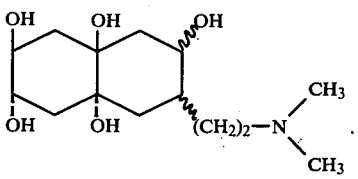

12. The compound according to claim 1 wherein $R_1$, $R_2$, $R_3$ and $R_4$ are acyl and $R_5$ is hydroxy.

13. The compound according to claim 12 having the structure

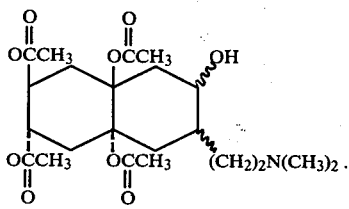

14. A pharmaceutical composition for use in the treatment of hypertension comprising an effective amount of a compound as defined in claim 1 and a pharmaceutically acceptable carrier therefor.

15. A method of treating hypertension in mammalian species, which comprises administering to a mammalian host a therapeutic amount of the composition as defined in claim 14.

* * * * *

UNITED STATES PATENT OFFICE
CERTIFICATE OF CORRECTION

Patent No. 4,156,723          Dated May 29, 1979

Inventor(s) Frederic P. Hauck et al.

It is certified that error appears in the above-identified patent and that said Letters Patent are hereby corrected as shown below:

Column 1, structure I should read as follows:

-- 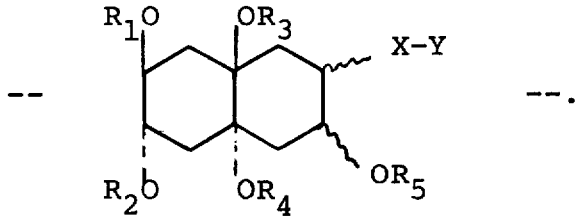 --.

Column 1, line 65, "sensciolo" should read --senecoic--.
Column 1, last line, before "butyric" insert --propionic, α-phenyl--.
Column 3, line 23, "aminomethyll-" should read --aminomethyl- --.
Column 3, line 35, "piperazinol" should read --piperazino--.
Column 3, line 38, "alkosy" should read --alkoxy--.
Column 3, last line, ";lower" should read --lower--.
Column 4, line 21, "such a" should read --such as--.
Column 4, line 32, "iodidel" should read --iodide;--.
Column 4, line 56, before "X-Y" insert -- ∿∿ --.
Column 4, line 57, before "OR$_5$" insert -- ∿∿ --.
Column 5, structure IV should read as follows:

-- 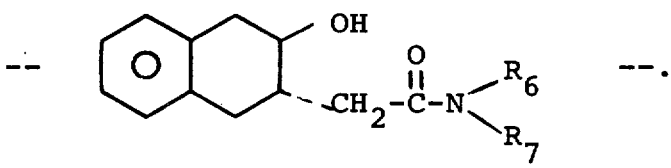 --.

UNITED STATES PATENT OFFICE
CERTIFICATE OF CORRECTION

Patent No. 4,156,723  Dated May 29, 1979

Inventor(s) Frederic P. Hauck et al.

It is certified that error appears in the above-identified patent and that said Letters Patent are hereby corrected as shown below:

Column 5, structure V should read as follows:

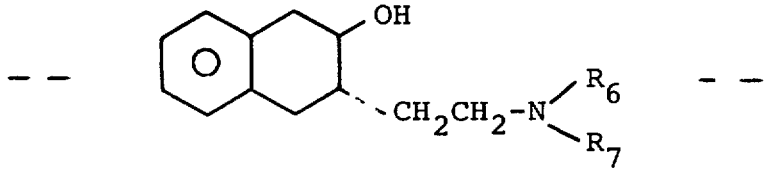

Column 5, line 35, after "reacting" insert --V--.
Column 6, structure XI should read as follows:

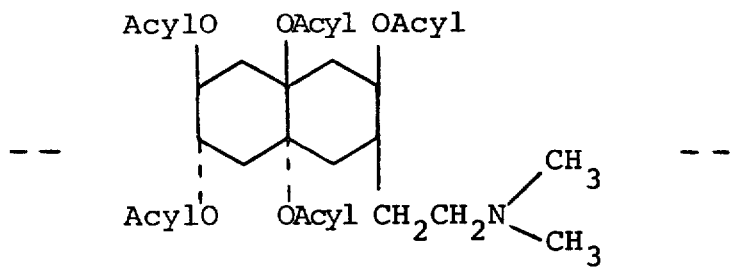

Column 6, structure XII should read as follows:

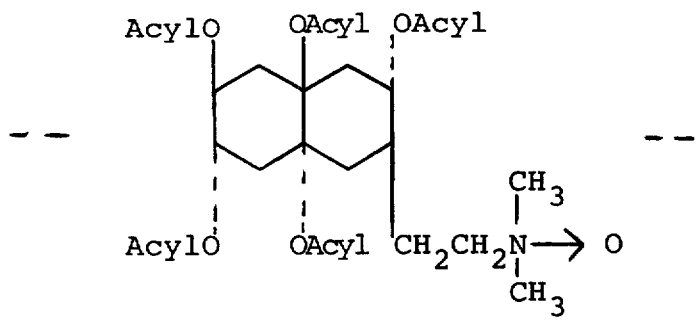

UNITED STATES PATENT OFFICE
CERTIFICATE OF CORRECTION

Patent No. 4,156,723      Dated May 29, 1979

Inventor(s) Frederic P. Hauck et al.

It is certified that error appears in the above-identified patent and that said Letters Patent are hereby corrected as shown below:

Column 11, structure XXVIII should read as follows:

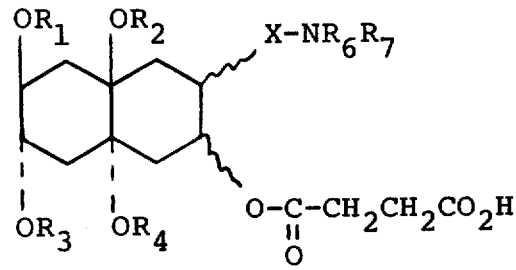

Column 11, structure XXIX should read as follows:

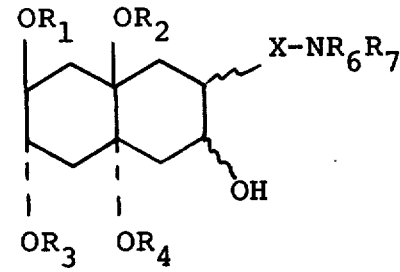

Column 12, line 32, "furan2" should read --furan-2--.
Column 15, line 2, "2,6,9a" should read --2,6,8a--.
Column 15, line 58, "dimethylamino2" should read --dimethylamino-2--.
Column 16, line 21, "isopropaneol" should read --isopropanol--.
Column 16, line 57, "8hexahy" should read --8-hexahy--.
Column 17, line 11, "yield" should read --yielded--.
Column 17, line 24, "2,34a," should read --2,3,4a,--.
Column 17, line 27, "assed" should read --added--.
Column 17, line 34, before "extracts" delete the word "and".
Column 16, line 54, "8-a" should read --8a--.

UNITED STATES PATENT OFFICE
CERTIFICATE OF CORRECTION

Page 4 of 4

Patent No. 4,156,723                    Dated May 29, 1979

Inventor(s) Frederic P. Hauck et al.

It is certified that error appears in the above-identified patent and that said Letters Patent are hereby corrected as shown below:

Column 17, line 44, "19 1 ml" should read --19 ml--.
Column 17, line 46, "120°-120+°" should read --120°-130°--.
Column 19, line 6, after "6.4 g" insert --of--.
Column 19, line 27, "pf" should read --of--.

Signed and Sealed this

Twenty-fifth Day of September 1979

[SEAL]

Attest:

LUTRELLE F. PARKER
Attesting Officer     Acting Commissioner of Patents and Trademarks